(12) United States Patent
Larsson

(10) Patent No.: US 7,283,875 B2
(45) Date of Patent: Oct. 16, 2007

(54) NERVE STIMULATION DEVICE

(75) Inventor: Åke Larsson, Järfälla (SE)

(73) Assignee: Maquet Critical Care AB, Solna (SE)

( * ) Notice: Subject to any disclaimer, the term of this patent is extended or adjusted under 35 U.S.C. 154(b) by 384 days.

(21) Appl. No.: 10/638,151

(22) Filed: Aug. 8, 2003

(65) Prior Publication Data

US 2004/0044377 A1    Mar. 4, 2004

(30) Foreign Application Priority Data

Aug. 28, 2002 (SE) .................................. 0202537

(51) Int. Cl.
*A61N 1/08* (2006.01)
(52) U.S. Cl. .................... 607/42; 607/46; 607/124; 600/546; 600/547
(58) Field of Classification Search ................ 607/42, 607/20, 124, 46; 600/546, 547; 128/200.24
See application file for complete search history.

(56) References Cited

U.S. PATENT DOCUMENTS

| 5,016,647 A | 5/1991 | Sanders |
| 5,036,848 A | 8/1991 | Hewson |
| 5,671,752 A | 9/1997 | Sinderby et al. |
| 5,911,218 A | 6/1999 | DiMarco |
| 6,198,970 B1 | 3/2001 | Freed et al. |
| 6,234,985 B1* | 5/2001 | Lurie et al. ................... 601/41 |
| 6,360,740 B1 | 3/2002 | Ward et al. |
| 6,411,843 B1 | 6/2002 | Zarychta |
| 2002/0032468 A1* | 3/2002 | Hill et al. ..................... 607/2 |

FOREIGN PATENT DOCUMENTS

| WO | WO97/38751 | 10/1997 |
| WO | WO 00/00245 | 1/2000 |

* cited by examiner

*Primary Examiner*—Carl Layno
*Assistant Examiner*—Deborah Malamud
(74) *Attorney, Agent, or Firm*—Schiff Hardin LLP

(57) ABSTRACT

A nerve stimulation device has a pulse generator for generating stimulation pulses and an output for the stimulation pulses from the pulse generator, which is connectable to an electrode arrangement adapted for interaction with a living being to stimulate the phrenic nerve. The nerve stimulation device is made more safe and effective by the provision of an input connectable to an esophageal electrode for the reception of measurement signals. The esophageal electrode is adapted to be inserted in the esophagus of the living being for obtaining measurement signals. A signal analyzer filters myo-electrical signals from the diaphragm out of the measurement signals and a regulating unit regulates the pulse generator dependent on the myo-electrical signals.

5 Claims, 2 Drawing Sheets

NERVE STIMULATION DEVICE

BACKGROUND OF THE INVENTION

1. Field of the Invention

The present invention relates to a nerve stimulation device for stimulating the phrenic nerve of a living subject.

2. Description of the Prior Art

A number of different methods exist for treatment of breathing difficulties. Positive pressure ventilation using a ventilator or respirator is probably the most common method today. It has in principle completely replaced negative pressure ventilation (for example, the iron lung). Stimulation of breathing musculature and the stimulation of nerves related to breathing (especially the phrenic nerve) are known but, in practice, are not used to any great extent.

Various systems for nerve stimulation are described in, for example, PCT Application WO 97/38751 and U.S. Pat. No. 6,360,740. These primarily describe electrical stimulation but it also is known to use magnetic stimulation in order to stimulate nerves.

Nerve stimulation makes heavy demands on functionality to make it as safe and as reliable as possible. The phrenic nerve, for example, is situated near the vagus nerve. Stimulation of the vagus nerve can lead to a slowing of heart activity (bradycardia). Transcutaneous stimulation therefore requires sensitivity in the placement of the electrode, so that only the phrenic nerve is stimulated. A subcutaneous connection to the phrenic nerve, of course, does not present this problem, but a surgical intervention is necessary. Moreover, it is not a simple matter to isolate the phrenic nerve with a surgical intervention. As with all surgical interventions there is the risk that surrounding tissue or nerves will be damaged or affected.

Another problem with nerve stimulation is the choice of stimulation energy necessary to achieve a sufficient response in the musculature of the breathing system (with stimulation of the phrenic nerve it is primarily the diaphragm that is involved).

It would be an advantage if a method of nerve stimulation could be developed in which a physiologically more natural effect resulted and with fewer negative side effects on the patient than with positive pressure ventilation.

SUMMARY OF THE INVENTION

An object of the present invention is to produce a nerve stimulation device for stimulating the phrenic nerve via an electrode arrangement at least partially solves some of the described problems.

The above object is achieved in accordance with the principles of the present invention in a nerve stimulator having a pulse generator and an electrode arrangement adapted to deliver stimulation pulses to stimulate the phrenic nerve, and having an esophageal electrode adapted for insertion in the esophagus of the subject for obtaining measurement signals, and a signal analyzer supplied with the measurement signals that filters myo-electrical signals originating from the diaphragm out of the measurement signals, and a regulation unit which regulates the pulse generator dependent on the myo-electrical signals.

The electrode arrangement can be a subcutaneous electrode arrangement or a transcutaneous electrode arrangement.

The diaphragm is the primary motor driving force for breathing. When the diaphragm functions it emits myo-electrical signals (EMG) in proportion to the effect of the work. EMG measurement therefore gives a measure of the effect of the stimulation of the phrenic nerve. EMG activity in the diaphragm may be measured using, for example, a method described in U.S. Pat. No. 5,671,752. This method primarily involves an electrode arrangement that is conducted through the esophagus so that some of the electrodes pass the center of the diaphragm. The EMG activity in the diaphragm can be determined both qualitatively and quantitatively by means of special filtering and combination of signals from electrodes on either side of the center of the diaphragm.

In the nerve stimulation device according to the invention EMG is employed as a feedback signal that is used for the regulation of the stimulation signal. An optimal form of the stimulation signal may then be established. Through the use of an electrode arrangement having a number of electrodes for nerve stimulation (or by moving the existing electrode (s)) the best placement for stimulation may be determined.

In order to avoid effects on the heart the nerve stimulation device may be designed so that heart signals (ECG) are filtered from the measurement signal that is recorded by the esophageal electrode. Shaping of the stimulation pulses, as well as the placement of the electrodes, thus can be optimized even with regard to effects on the heart.

Alternatively, signals related to the heart activity may be transferred from a suitable apparatus for the acquisition of such information (surface-ECG, pulse meter, etc.).

An additional monitoring of the effect of the stimulation may be obtained by monitoring whether the patient actually breathes. This may be achieved by the nerve stimulation device registering signals from one or several other units. One example is a ventilator, for example a ventilator that maintains a constant positive pressure, CPAP, to facilitate the supply of air/breathing gas to the patient. The ventilator normally includes monitoring of the flow, pressure, etc., that can be used by the nerve stimulation device to monitor the breathing.

Other units that can indicate a patient's breathing are spirometry, measurement of impedance in the thorax (for example by means of impedance tomography, EIT), measurement of the circumference of the thorax (for example by means of optical fibers placed around the thorax), measurement of $CO_2$ content in breathing gas (for example a gas analyzer), measurement of $CO_2$ in blood (for example the transcutaneous measurement of venous blood), etc. A combination of several of these may also be employed.

DESCRIPTION OF THE PREFERRED EMBODIMENTS

Figure 1:
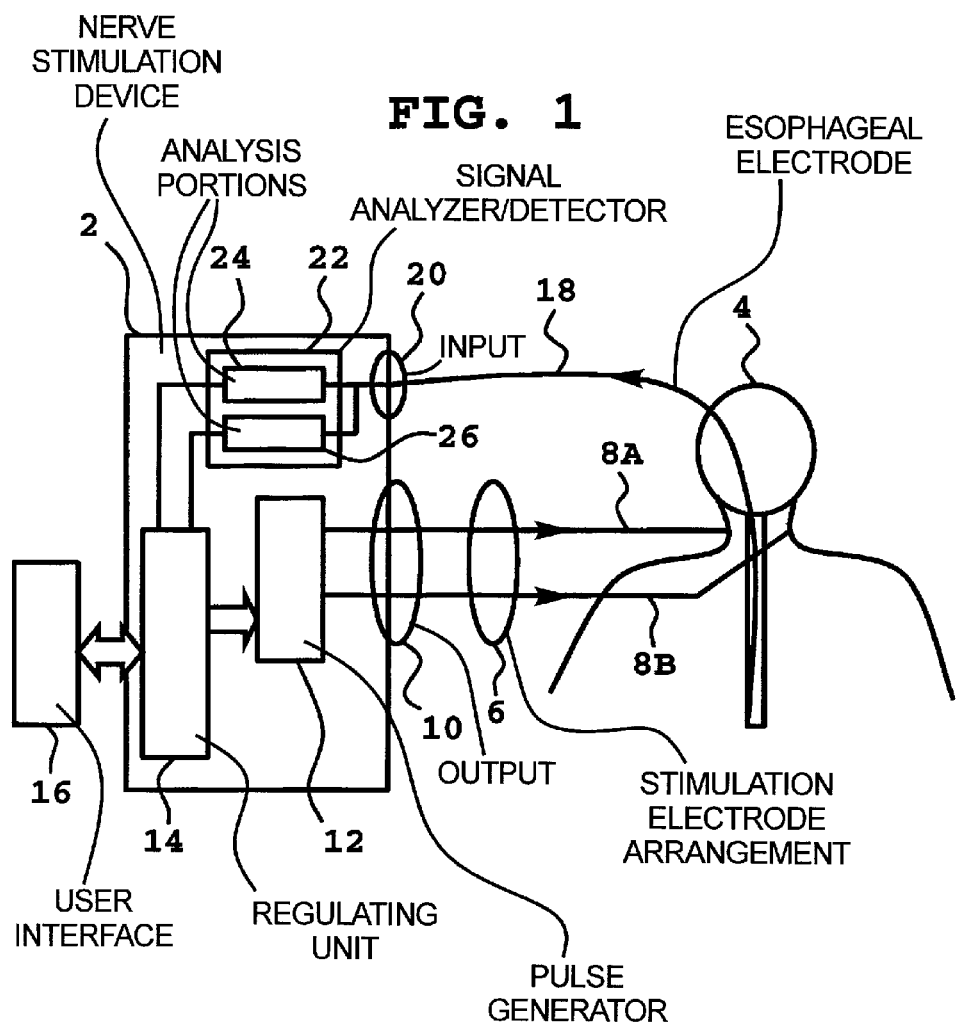
FIG. 1 shows a first exemplary embodiment of a nerve stimulation device according to the present invention.

The nerve stimulation device 2 can be connected to a patient 4 for stimulation of the phrenic nerve of the patient 4 via an electrode arrangement 6. In the present example the electrode arrangement 6 includes a first electrode 8A and a second electrode 8B, intended for placement on each side of the neck of the patient 4. The connection may be done for transcutaneous or subcutaneous stimulation. The electrode arrangement 6 is connected in use to an output 10 of the nerve stimulation device 2.

The nerve stimulation device 2 has a pulse generator 12 that generates stimulation pulses and delivers these to the output 10. The pulse generator 12 is controlled by a regulating unit 14.

A user interface 16 is provided to enable a user to choose functions, program the operating mode, obtain information about stimulation, etc. The user interface 16 may have a screen, a keyboard, etc. The user interface 16 does not necessarily have to be an integrated part of the nerve stimulation device 2. It may, for example, be a computer (for example a PC) or other freestanding apparatus. It is also possible to have a combination with a simplified user interface on the nerve stimulation device 2 itself with the capability to connect a more advanced user interface as required (not shown in the figure). The design of the user interface 16 thus does not necessarily differ from known designs of a user interface. The user interface 16 does not therefore require a further, more detailed description as it is known to those skilled in the art how it can be provided.

To optimize the functioning of the nerve stimulation device 2 myo-electrical signals from the diaphragm are detected. An esophageal electrode 18 is connected to an input 20 of the nerve stimulation device 2 for this purpose. It should be noted that the input 20 has several channels, one for each lead in the esophageal electrode 18.

A signal analyzer 22 is provided in the nerve stimulation device 2 and filters the myo-electrical signals from the raw signals. More precisely, the signal analyzer 22 has a first analysis portion 24 for this purpose. The signal analyzer 22 further has a second analysis portion 26, the purpose of which will be described below.

It is known to record signals from the diaphragm and extract myo-electrical signals (EMG) therefrom. Such a method is described in U.S. Pat. No. 6,360,740. This also does not need to be described in more detail in connection with the present invention.

The obtained EMG response is a measure of the effectiveness of the stimulation pulse or pulses in producing a contraction of the diaphragm. This contraction results in the patient 4 taking a breath. The obtained EMG response is supplied to the regulation unit 14 where the stimulation pulse is optimized.

By varying the energy content of the stimulation pulse a desired breathing effect (response in the EMG) can be obtained. The energy content can be varied by variations of the pulse duration, amplitude, etc. One or several pulses can also be used as a suitable variable.

By compiling data from a large number of patients a database of signals can be constructed from which appropriate levels of stimulation energy, EMG response, etc, can be extracted.

Another suitable parameter is the placement of the electrode 8A, 8B on the patient 4. Stimulation may be effected via one or several electrodes 8A, 8B simultaneously or sequentially. A test with these variables can lead to a more optimal stimulation effect. Even more electrodes can be placed along the phrenic nerve in order to identify the best placement.

Since the vagus nerve is near to the phrenic nerve, the risk of the stimulation also affecting the vagus nerve exists. This can lead to a slowing of heart activity (bradycardia). To avoid this the second analysis portion 26 filters the heart related signals from the raw signals at the input 20. In principle the entire cardiogram (ECG) can be extracted from the raw signal in a known way, but for many applications and monitoring of the heart's frequency a filtering of the R-wave in the ECG may be sufficient. The R-wave is the dominant component of an ECG.

The filtered heart signal is transferred to the regulating unit 14, which uses the heart signal as an additional parameter in the optimization of the stimulation. The permitted or allowable effects on the heart activity may be decided individually from case to case or in advance as a certain percentage of the patient's normal heart frequency, for example, within the interval 0-20% or some other interval. In principle the invention optimizes the stimulation location and stimulation energy as variable parameters within predetermined boundaries to maximize EMG response and minimize the effect on the heart. Known algorithms and methods for optimization can easily be applied by those skilled in the art and tested.

It is evident that instead of filtering heart signals from the measurement signals from the esophageal electrode, information from an ECG apparatus or the equivalent can be transferred to the regulating unit 14 with the same effect. A normal surface ECG may be used. Even a simple pulse meter can give information about changes in the heart activity that can be used as a parameter.

Figure 2:
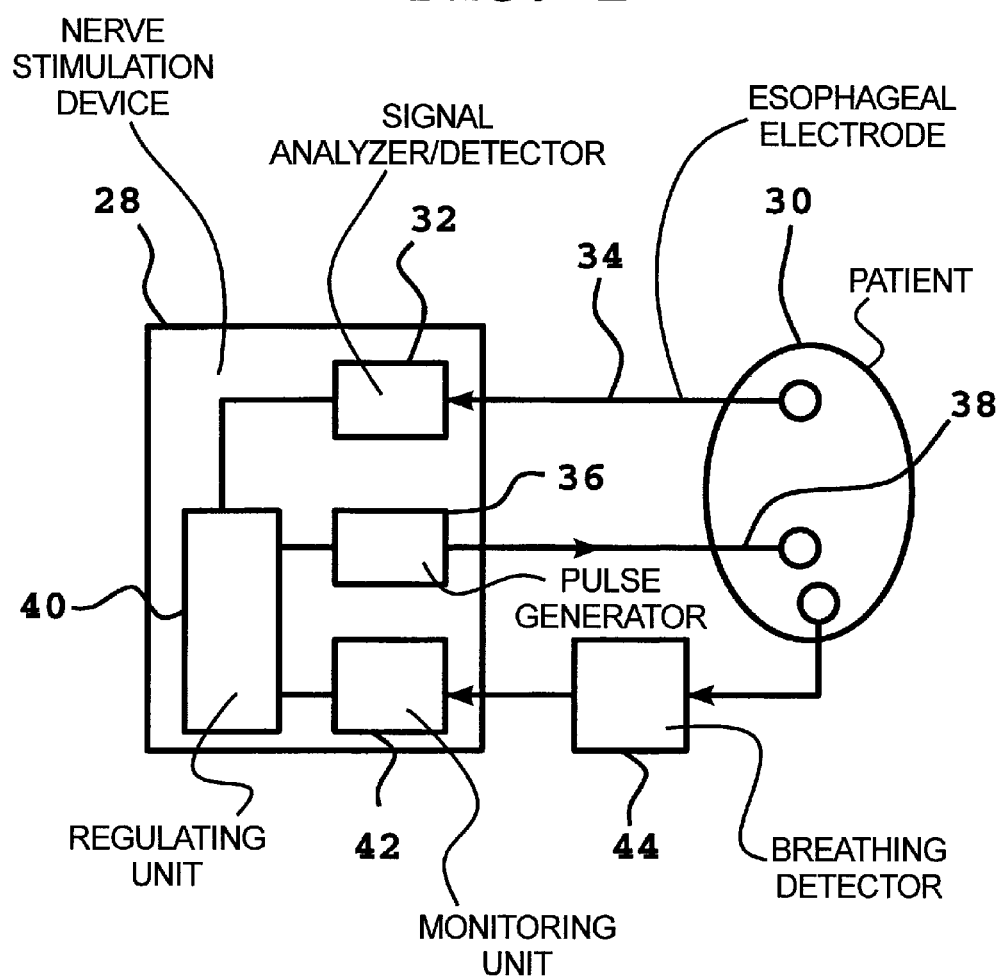
FIG. 2 shows a second exemplary embodiment of a nerve stimulation device according to the present invention.

In FIG. 2 a second exemplary embodiment of a nerve stimulation device 28 according to the present invention is shown. The nerve stimulation device 28 is connectable to a patient 30.

In common with the previous exemplary embodiment, a signal analyzer 32 is arranged to filter the EMG response from the patient 30 from a raw signal from an esophageal electrode 34. A pulse generator 36 is likewise arranged to generate and emit stimulation pulses to the patient 30 via an electrode arrangement 38. In this regard a regulating unit 40 controls the pulse generator 36 dependent on the EMG response obtained via the signal analyzer 32.

In the second exemplary embodiment the nerve stimulation device 28 is also equipped with a monitoring unit 42. The purpose of the monitoring unit 42 is to provide the patient 30 with additional safety and to ensure that breathing actually occurs in accordance with the EMG response.

To this end, the monitoring unit 42 receives a measurement signal from a breathing detector 44, which is arranged in a suitable manner to generate a signal reflecting the breathing of the patient.

The device 44 may be a ventilator or respirator that can deliver a constant airways pressure, CPAP. Such a ventilator is the Servo ventilator 300, available from Siemens Elema AB, Sweden. Such a ventilator can give an output in the form of a flow measurement, valve regulation, etc., that provides a measure of the breathing of the patient 30.

Alternatively, the device 44 may be a simple spirometer through which the patient 30 can breathe. In principle the spirometer may be formed of a tube having a flow meter. Such spirometers are known components to those skilled in the art and need no further description.

As a further alternative the device 44 may be configured to measure impedances in the thorax (rib cage) of the patient 30 in order to determine breathing. One way to achieve this is described in U.S. Pat. No. 6,015,389. Those skilled will be aware of still further ways, so it is not essential to provide details of this feature in connection with the present application.

An additional alternative is to configure the device 44 to determine the circumference of the thorax of the patient 30 as a way of identifying breathing. Several methods for the indirect determination of the circumference of the thorax (via the lung volume) are found in U.S. Pat. No. 5,937,854. Other methods will be apparent to those skilled in the art.

The device 44 may be a gas analyzer that is arranged to determine an exhaled carbon dioxide level. The exhaled carbon dioxide level is a measure of the lungs' ventilation and thereby the breathing of the patient 30. Gas analyzers are well known and employed within the field of ventilation. Other gas measurements are also suitable, for example the difference in oxygen concentration between inhalation and exhalation, which is a measure of gas exchange within the lungs, or the supply and measurement of a trace gas or the addition of a substance to the body that secretes a measurable gas component to the exhalation gas in the lungs.

A further alternative for the device 44 to be designed is to determine the level of carbon dioxide or oxygen in the blood. This may be achieved either by transcutaneous (oximeter) or subcutaneous (invasive) measurement with a blood gas analyzer.

Other known ways to determine if the patient 30 breathes may also be employed.

The two embodiments that are provided above may be combined in any suitable way to achieve the functionality of the invention.

Although modifications and changes may be suggested by those skilled in the art, it is the intention of the inventor to embody within the patent warranted hereon all changes and modifications as reasonably and properly come within the scope of his contribution to the art.

I claim as my invention:

1. A nerve stimulation device comprising:

a pulse generator which generates stimulation pulses;

an electrode arrangement connected to the pulse generator configured to interact with a living subject to deliver the stimulation pulses to stimulate the phrenic nerve;

a cardiac signal detector configured to obtain an ECG signal from the living subject indicative of a degree of stimulation of the vagus nerve of the living subject associated with the stimulation of the phrenic nerve by said stimulation pulses; and a regulating unit connected to said cardiac signal detector and to said pulse generator for regulating the pulse generator dependent on the ECG signal to reduce said degree of stimulation of the vagus nerve by said stimulation pulses.

2. A nerve stimulation device as claimed in claim 1 further comprising a monitoring unit configured to interact with the living subject to monitor breathing of the living subject and which generates a monitoring unit output supplied to said regulating unit, said regulating unit regulating the pulse generator dependent on said monitoring unit output as well as dependent on said ECG signal.

3. A nerve stimulation device as claimed in claim 2 wherein said monitoring unit comprising a breathing detector selected from the group consisting of an external ventilator, a spirometer, an impedance measurement arrangement, a thorax circumference measurement arrangement, and a gas analyzer.

4. A nerve stimulation device as claimed in claim 1 wherein said electrode arrangement comprises a plurality of electrode leads and wherein said pulse generator is connected to said electrode arrangement via an output interface comprising a plurality of channels, with one channel for each electrode lead, and wherein said regulating unit regulates said pulse generator to individually control delivery of stimulation pulses via the respective electrode leads.

5. A nerve stimulation device as claimed in claim 1 wherein said cardiac signal detector comprises:

an esophageal electrode adapted for insertion in the esophagus of the living subject for obtaining measurement signals; and a signal analyzer connected to the esophageal electrode for filtering said ECG signal, from said measurement signals.

* * * * *